United States Patent [19]
Pettit et al.

[11] Patent Number: 5,599,902
[45] Date of Patent: Feb. 4, 1997

[54] CANCER INHIBITORY PEPTIDES

[75] Inventors: George R. Pettit, Paradise Valley; Jayaram K. Srirangam, Tempe, both of Ariz.

[73] Assignee: Arizona Board of Regents acting on behalf of Arizona State University, Tempe, Ariz.

[21] Appl. No.: 338,004

[22] Filed: Nov. 10, 1994

[51] Int. Cl.$^6$ ................ C07K 5/00; C07K 7/00; C07K 17/00; A61K 38/00
[52] U.S. Cl. ................ 530/330; 530/331
[58] Field of Search ................ 530/330, 331; 514/17, 18

[56] References Cited

U.S. PATENT DOCUMENTS 5,502,032  3/1996  Haupt et al. ................ 514/17
5,504,191  4/1996  Pettit et al. ................ 530/330

*Primary Examiner*—Michael P. Woodward
*Assistant Examiner*—Benet Prickril
*Attorney, Agent, or Firm*—Richard R. Mybeck

[57] ABSTRACT

The sea hare *Dolabella auricularia* has yielded many structurally distinct peptides which possess antineoplastic activity. Presently the compound denominated "dolastatin 10" represents the most important of such peptides because of its demonstrated potential as an anticancer drug.

The present invention relates to the systematic creation of seven unique pentapeptides by selectively coupling a tripeptide-trifluoroacetate salt with a preselected dipeptide trifluoroacetate salt which provide active molecules capable of emulating the measured therapeutic effect of dolastatin 10.

7 Claims, 1 Drawing Sheet

CANCER INHIBITORY PEPTIDES

Financial assistance for this project was provided by the National Cancer Institute, Grant Number 01G-CA44344-01-04-05 and the United States Government may own certain rights to this invention.

INTRODUCTION

This invention relates generally to the field of peptides useful in chemotherapy and more particularly to the elucidation and synthesis of selected peptides which are structurally related to dolastatin 10. More particularly, the present invention relates to the synthesis of seven pentapeptides by coupling dipeptide salts with the known tripeptide-trifluoroacetate salt to provide compounds which are found to exhibit effective antineoplastic activity against various of the human cancer tumor cell lines currently employed by the National Cancer Institute.

BACKGROUND OF THE INVENTION

Ancient marine invertebrate species of the *Phyla Bryozoa, Molluska,* and *Porifera* have been well established in the oceans for over one billion years. Such organisms have undergone trillions of biosynthetic reactions in their evolutionary chemistry to reach their present level of cellular organization, regulation and defense.

Marine sponges, for example, have changed minimally in their physical appearance over the last 500 million years. This suggests a very effective chemical resistance to evolution in response to changing environmental conditions over that period of time. Recognition of the potential for utilizing this biologically potent marine animal for medicinal purposes was recorded in Egypt about 2,700 B.C. and by 200 B.C. sea hare extracts were being used in Greece for their curative affect. This consideration along with the observation that marine animals, e.g., invertebrates and sharks, rarely develop cancer led to the systematic investigation of marine animal and plant anticancer compounds.

By 1968 ample evidence had been obtained, based on the U.S. National Cancer Institute's (NCI) key experimental cancer study systems, that certain marine organisms could provide new and antineoplastic and/or cytotoxic agents and might also lead to compounds which would be effective in the control and/or eradication of viral diseases. Further, these marine organisms were believed to possess potentially useful drug candidates of unprecedented structure which had eluded discovery by other methods of medicinal chemistry. Fortunately, these expectations have been realized, e.g., the discovery of the bryostatins, dolastatins and cephalostatins, many of which are now in preclinical development or human clinical studies.

Those researchers presently involved in medicinal chemistry know well the time lag between the isolation of a new compound and its introduction to the market. This procedure takes several years and often takes decades. Accordingly, industry, in association with the U.S. Government, has developed a system of testing criteria which serves two purposes. One is to eliminate those substances which are shown through testing to be economically counterproductive. The second, more important purpose serves to identify those compounds which demonstrate a high likelihood of success and therefore warrant the further study and qualification, and attendant expense, necessary to meet the stringent regulatory requirements which control the ultimate market place.

The current cost to develop this necessary data approaches ten million dollars per compound. Such a large investment will be made only when there is a reasonable opportunity for it to be recovered. Absent such opportunity, there will be no investment and the research involving the discovery of these potentially life saving compounds will cease.

Only two hundred years ago many diseases ravaged mankind. Many of these now have been controlled or eradicated. During the advancement of means to treat or eliminate these diseases, work with appropriate animals was of critical importance.

Current research in the control of cancer in the United States is coordinated by the National Cancer Institute (NCI). To determine whether a substance has anti-cancer properties, the NCI has established a systematic protocol. This protocol, which involves the testing of a substance against a standard cell line panel containing 60 human tumor cell lines, has been verified and has been accepted in scientific circles. The protocol, and the established statistical means for analyzing the results obtained by the standardized testing are fully described in the literature. See: Boyd, Dr. Michael R., *Principles & Practice of Oncology,* PPO Updates, Volume 3, Number 10, October 1989, for a general overview of the testing protocol; Monks, Anne et al., "Feasibility of a High-Flux Anticancer Drug Screen Using a Diverse Panel of Cultured Human Tumor Cell Lines", 83 *J. Nat. Cancer Inst.* No. 11, 757 (1991); and Paull, K. D., "Display and Analysis of Patterns of Differential Activity of Drugs Against Human Tumor Cell Lines; Development of Mean Graph and COMPARE Algorithm", *J. of the Nat. Cancer Inst. Reports,* Vol 81, No. 14, Page 1088, Jul. 14, 1989, for a description of the methods of statistical analysis. Each of these references are incorporated herein by this reference thereto.

Numerous substances have been discovered which demonstrate significant antineoplastic or tumor inhibiting characteristics. As stated above, many of these compounds have been extracted, albeit with great difficulty, from marine animals such as the sponge and sea hare. Once isolation and testing of these compounds has been accomplished, a practical question remains, namely how to produce commercially significant quantities of the desired substance.

Quinine, which is available in practical quantities from the bark of the cinchona plant, differs from the compounds which are extracts of marine creatures possessing antineoplastic qualities. The collection and processing of these latter compounds from their natural sources ranges from grossly impractical to the utterly impossible. Ignoring the ecological impact of such harvesting, the population of these creatures and the cost of collection and extraction make the process unworkable. Artificial synthesis of the active compounds is the only possible solution.

The Constitution of the United States (Art. 1, Sec. 8) authorized Congress to establish the United States Patent and Trademark Office (USPTO) to promote scientific progress. In order to obtain patent rights, one must show the utility of the invention. Cancer cell growth in humans often causes pain, suffering, and premature death. The impairment of human cancerous tumor growth is utilitarian in that it relieves these conditions, thereby allowing the human thus affected to have a longer, more productive life. Little could be more utilitarian than this result.

The sole right obtained from the grant of a Letters Patent is to prevent others from exploiting the subject matter of the patent. This results in the protection of the inventor for a period adequate to allow the recoupment of investment. This in turn provides incentive for further research.

The recognition of antineoplastic and tumor inhibiting activity as demonstrated by accepted NCI criteria as "utility" can promote research efforts in the United States and is unequivocally essential if those efforts are to obtain even a modest modicum of success.

BRIEF SUMMARY OF THE INVENTION

The synthesis of potentially useful peptides presents one of the most essential and promising approaches to new types of anticancer drugs. The Dolastatins, an unprecedented series of linear and cyclic antineoplastic and/or cytostatic peptides isolated from the Indian Ocean sea hare *Dolabella auricularia* represent excellent leads for invention of new and strongly cell growth inhibitory peptides. The very productive sea hare *Dolabella auricularia* has produced a number of structurally distinct peptides with excellent antineoplastic activity. Presently Dolastatin 10, a linear pentapeptide, represents the most important member of the dolastatin family and is a potentially useful antineoplastic agent. Dolastatin 10 shows one of the best antineoplastic activity profiles against various cancer screens exhibited to date.

The complicated structure of dolastatin 10 and the difficulties involved in its synthesis encourages the search for simpler peptides with comparable or stronger activities. Such discoveries would greatly help in reducing the cost of such anticancer drugs. One of the approaches to invention of such simpler compounds is by molecular modeling. This method has been incorporated in the design and the synthesis of new and potent peptides. Prior modeling efforts with (6R)-isodolastatin 10 greatly assisted this research.

Figure 1:
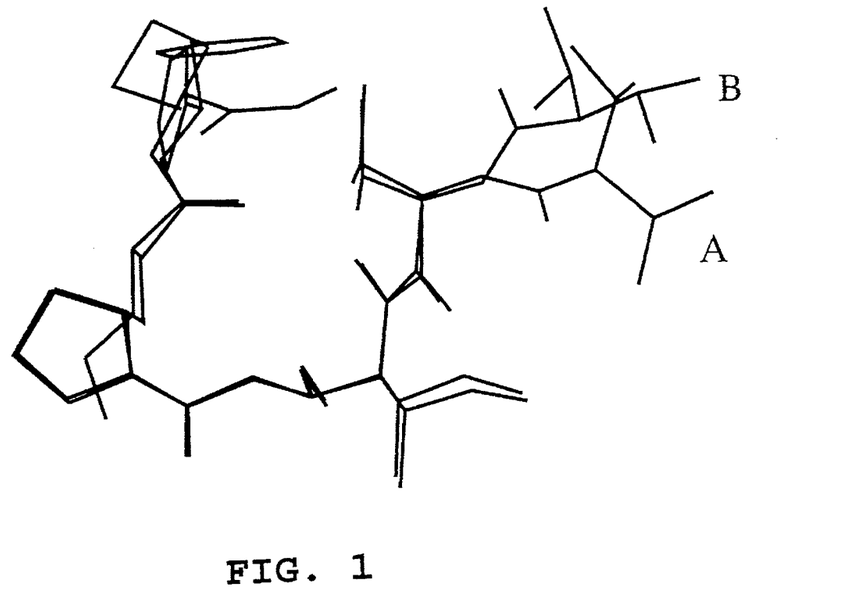
FIG. 1 is a overlay of cis-(6R)-isodolastatin 10 with cis-dov-val-dil-desmethoxy-desmethyl-dolaproine-methionine methyl ester.
Figure 2:
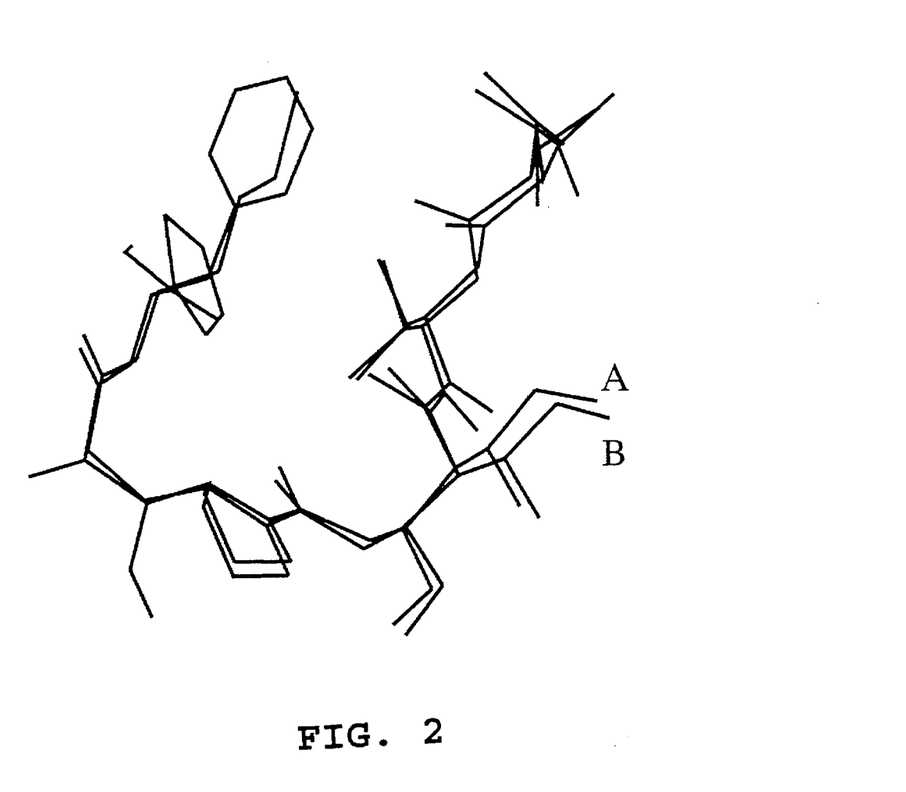
FIG. 2 is a overlay of trans-(6R)-isodolastatin 10 with trans-dov-val-dil-desmethoxy-desmethyl-dolaproine-methionine methyl ester.

A molecule (22c) was designed based on the conformational similarities with (6R)-isodolastatin 10 (See FIGS. 1a and 1b). The molecule was then synthesized by the procedure outlined in this application. The compound thus obtained showed significant activity against the L1210murine leukemia cells (IC$_{50}$: Dolastatin 10=1 µM; 22c=4 µM). Importantly in the new compound 22c, the complicated and difficult to synthesize dipeptide unit A of dolastatin 10 is replaced by a simpler and easily synthesizable dipeptide unit B.

The compounds disclosed herein are new and useful structural modifications of dolastatin 10. This research has led to an effective method for the synthesis of new and very potent anticancer peptides related in structure to dolastatin 10. The present invention involves the synthesis of seven such peptides as shown below to provide viable alternatives for dolastatin 10.

Accordingly, the primary object of the present invention is to provide the elucidation and synthesis of seven new peptide derivatives of dolastatin 10, each of which exhibits effective antineoplastic activity against various human cancer and mouse leukemia (P-388) cell lines.

Another object of the present invention is to provide novel substances which are therapeutic equivalents to dolastatin 10 and which can be created by economically viable procedures in commercially viable quantities.

These and still further objects as shall hereinafter appear are readily fulfilled by the present invention in a remarkably unexpected manner as will be readily discerned from the following detailed description of an exemplary embodiment thereof.

DESCRIPTION OF THE PREFERRED EMBODIMENT

STATISTICAL DEFINITIONS

The following measures are used to express drug activity by giving the drug dose which reduces cell growth to a specified percentage of growth:

ED$_{50}$ (P-388) and GI$_{50}$ (HTCL) are the drug doses needed to reduce the percent growth to 50%. There is no mathematical difference between ED$_{50}$ and GI$_{50}$, which are both calculated using the same formula. The only difference is historical usage.

TGI, (Total Growth Inhibition), is the drug dose needed to yield zero percent growth, i.e., just as many cells at the end of the experiment as were present in the beginning. Whether just as many cells were killed as were produced (steady state), or no growth occurred (total inhibition), cannot be distinguished.

LC$_{50}$, (Lethal Concentration 50%), is the drug concentration which reduces growth to –50%, i.e., removes half of the cells originally present at the beginning of the experiment.

Each drug is tested at five (5) doses: 100–10–1–0.1–0.01 µg/ml. Percent Growths are calculated for each dose. The two (or three) doses with growth values above, below, (or near to) 50% growth are used to calculate the ED$_{50}$/GI$_{50}$ using a linear regression formula. The log of the dose is used during the regression computation. If no dose yields a growth value under 50%, the results are expressed as: ED$_{50}$>(highest dose). If no dose yields growth higher than 50% growth, then ED$_{50}$<(lowest dose). Similar calculations are performed for the TGI at 0% growth, and at –50% growth for the LC$_{50}$.

PERCENT OF GROWTH

At the start of an experiment, cells from the in vitro cell cultures are inoculated into the appropriate tubes or microtiter plates. One set of control tubes/plates is immediately counted to determine the number of cells at the start of the experiment. This is the "baseline count" or "T$_{zero}$ reading". At the end of the experiment (48 hours later) a second set of control tubes/plates is analyzed to determine the "Control Growth" value. The growth (or death) of cells relative to the initial quantity of cells is used to define the "Percent of Growth".

| | Baseline Count = 20 Control Count = 200 (10-Fold Growth) |
|---|---|
| 100% Growth = Control Growth | 100% Growth = 200 |
| 50% Growth = $T_{zero} + \dfrac{Control - T_{zero}}{2}$ | 50% Growth = 110 |
| 0% Growth = $T_{zero}$ | 0% Growth = 20 |
| −50% Growth = $T_{zero}/2$ | −50% Growth = 10 |

The synthesis of potentially useful peptides presents one of the most essential and promising approaches to new types of anticancer and immunosuppressant drugs. The Dolastatins, an unprecedented series of linear and cyclic antineoplastic and/or cytostatic peptides isolated from Indian Ocean sea hare *Dolabella auricularia* represent excellent leads for synthetic modification. The very productive sea hare *Dolabella auricularia* has produced a number of structurally distinct peptides with excellent antineoplastic activity. Presently dolastatin 10, a linear pentapeptide represents the most important member and is a potentially useful antineoplastic agent. Dolastatin 10 shows one of the best antineoplastic activity profiles against various cancer screens presently known. Recently the total synthesis and absolute configuration of this structurally unique and biologically active peptide was reported. This compound has been tested in vivo and demonstrated significant activity, as shown below.

Experimental Anticancer Activity of Dolastatin 10 in Murine in vivo Systems, T/C (µg/kg)

| P388 Lymphocytic Leukemia | |
|---|---|
| toxic | (13.0) |
| 155 and 17% cures | (6.5) |
| 146 and 17% cures | (3.25) |
| 137 | (1.63) |
| L1210 Lymphocytic Leukemia | |
| 152 | (13) |
| 135 | (6.5) |
| 139 | (3.25) |
| 120 | (1.63) |
| B16 Melanoma | |
| 238 and 40% cures | (11.11) |
| 182 | (6.67) |
| 205 | (4.0) |
| 171 | (3.4) |
| 142 | (1.44) |
| M5076 Ovary Sarcoma | |
| toxic | (26) |
| 166 | (13) |
| 142 | (6.5) |
| 151 | (3.25) |
| LOX Human Melanoma Xenograft to (Nude Mouse) | |
| toxic | (52) |
| 301 and 67% cures | (26) |
| 301 and 50% cures | (13) |
| 206 and 33% cures | (6.5) |
| 170 and 17% cures | (3.25) |
| LOX in separate experiments | |
| 340 and 50% cures | (43) |
| 181 and 33% cures | (26) |
| 192 | (15) |
| 138 and 17% cures | (9.0) |
| Human Mammary Xenograft Nude Mouse | |
| Toxic | (26) |
| 137 | (13) |
| 178 | (6.25) |
| OVCAR-3 Human Ovary Xenograft Nude Mouse | |
| 300 | (40) |
| MX-1 Human Mammary Xenograft (Tumor Regression) | |
| 14 | (52) |
| 50 | (26) |
| 61 | (13) |
| 69 | (6.25) |

Dolastatin 10 has also been tested against a minipanel from the NCI Primary screen. These results appear below, showing the amount of dolastatin 10 required to attain $GI_{50}$ in µg/ml, against the cell lines set forth below.

| | |
|---|---|
| $\dfrac{OVCAR-3}{9.5 \times 10^{-7}}$ | (A) |
| $\dfrac{SF\ 295}{7.6 \times 10^{-8}}$ | (B) |
| $\dfrac{A498}{2.6 \times 10^{-5}}$ | (C) |
| $\dfrac{NC1-H460}{3.4 \times 10^{-6}}$ | (D) |
| $\dfrac{KM20L2}{4.7 \times 10^{-6}}$ | (E) |
| $\dfrac{SK-MEL-5}{7.4 \times 10^{-6}}$ | (F) |

From the foregoing, it can be seen that the in Vitro activity of dolastatin 10 in the primary screen has been confirmed by in vivo animal tests.

For the compounds disclosed in this application, the in vitro tests disclosed above are reasonably accurate predictors of anticancer activity, and not mere indicators of the desirability for further testing.

The synthesis of the new compositions involved the chemicals and reactions shown below. For convenience, compounds are generally referred to throughout by the arbitrary reference numerals assigned below:

a) R = H
b) R = CH₃ a) R = H
b) R = CH₃ a) R = H
b) R = CH₃

Ar = CH₂CH₂Ph

9
-continued
10 a) R = H
b) R = CH₃

Ar = CH₂CH₂Ph

-continued

The synthesis of the disclosed compounds involved the use of several General Procedures. These General Procedures are as set forth below.

General Procedure A

To a well stirred solution of the phosphorane (2, 0.0075M) in dry dichloromethane (15 mL) was added a solution of the prolinal (1, 0.0074M) in dichloromethane (10 mL), under argon atmosphere, slowly over a period of 15 minutes. The resulting solution was refluxed for 3 to 6.5 hours. Dichloromethane was distilled off under reduced pressure and hexane (25 mL) was added to it. The precipitated triphenylphosphine oxide was removed by filtration and the residue concentrated and chromatographed on a SILICA GEL column.

General Procedure B

To a solution of the ester (3a–b, 4, 0.88 mmol) in ethanol (5 mL) was added LiOH (1.76 mmol) in water (1 mL) and the solution was stirred at room temperature for 5 to 15 hours. Ethanol was distilled off and the residue taken into water (5 mL). The cooled aqueous layer was carefully acidified with dilute hydrochloric acid. The aqueous layer was extracted with dichloromethane. Upon drying and distillation (reduced pressure) of the dichloromethane layer, the required acid was obtained.

General Procedure C

To a suspension of the (L)-methionine methyl ester-hydrochloride salt (8, 0.1439 mmol) and the acid (5a–c, 0.15 mmol) in dry dichloromethane (1 mL), cooled to ice-bath temperature, was added triethylamine (3.5 eq.) followed by diethylphosphorocyanidate "DEPC" (1.1 eq.) under an argon atmosphere and the resulting solution was stirred at the same temperature for 1.5 hours. The precipitated triethylamine hydrochloride was filtered, solvent distilled off under reduced pressure and the residue chromatographed on a SILICA GEL column with suitable eluents to obtain the required dipeptides (9a–c).

General Procedure D

To a solution of the compounds (12, 3b, 7, 9a–c, 0.08mmol) in dry dichloromethane (0.5 mL), cooled in an ice-bath, was added trifluoroacetic acid (1 mL) and the solution was stirred at the same temperature under argon atmosphere for 2 hours. The solvents were then removed under reduced pressure. The oily residue was then taken into toluene (1 mL) and toluene was removed under reduced pressure. This operation was repeated again and the residue was dried under vacuum to obtain the free acid (13 in case of 12) or the trifluoroacetate salts (14–16) respectively in quantitative yields.

General Procedure E

To a suspension of the Dap-phenethylamine tfa salt (17, 0.03 mmol) and Z-val-dil free acid (13, 0.03 mmol) in dry dichloromethane (0.5 mL), cooled to ice-bath temperature, was added triethylamine (3.5 eq.) followed by diethylcyanophosphonate (1.1 eq.) under argon atmosphere and the resulting solution was stirred at the same temperature for 2 hours. The solvent was distilled off (reduced pressure) and the residue chromatographed over a SILICA GEL column with 2:3 hexane-acetone as the eluent to obtain the required tripeptide.

General Procedure F

To a suspension of the tripeptide-tfa salt (19, 0.13 mmol) and the tfa salts (14–16, 23, 0.12 mmol) in dry dichloromethane (1 mL), cooled to ice-bath temperature, was added triethylamine (3.5 eq) followed by diethylphosphorocyanidate (1.1 eq) under argon atmosphere and the resulting solution was stirred at the same temperature for 2 hours. The solvent was distilled off under reduced pressure and the residue chromatographed over a SILICA GEL column using suitable eluents to obtain the required peptides (20–22), (24).

As a first step two dolaproine derivatives were synthesized by the Wittig reaction of N-t-boc-prolinal with the phosphoranes (2) in dichloromethane. The phosphoranes selected were: ($\alpha$-carbethoxymethylidine)-triphenyl-phosphorane (2a); and ($\alpha$-carbethoxyethylidine)-triphenyl-phosphorane (2b). The transester (3b) was hydrogenated with Pd-C to obtain the saturated ester (4). Lithium hydroxide hydrolysis of the esters (3a–b, 4) led to the formation of the free acids (5a–c).

The esterification of N-t-boc-Dolaproine (6) was carried out with methyl iodide to form the methyl ester (7).

The modified N-t-boc amino acids (5a–c) were then coupled with methionine methyl ester (8) in presence of diethylphosphorocyanidate (DEPC) to form the respective dipeptides (9a–c). Similarly, t-boc-dolaproine (6) was coupled with phenethylamine (10) to form the amide (11).

The free acid z-N-Val-Dil-COOH (13) was prepared by the removal of the t-boc protecting group in (12) with trifluoroacetic acid.

The N-t-boc protecting group in the compounds (3b), (7), (9a–c) and (11) was removed with trifluoroacetic acid to yield the trifluoroacetate salts (14–17) respectively.

The dipeptide (13) was coupled with the trifluoroacetate salt of the amide (17) in presence of DEPC to form the tripeptideamide (18). Similarly the trifluoroacetate salts (14–16), and (23) were coupled with the tripeptide trifluoroacetate salt (19) in presence of DEPC to obtain the human cancer active peptides (20–22), (24) which demonstrate extraordinary inhibition of cell growth.

All these compounds (18), (20–22) and (24) have demonstrated outstanding efficacy as human cancer cell growth inhibitors. Various cancer cell growth inhibition tests for all these compounds is disclosed in TABLE 1.

TABLE 1

Human Cancer-Cell line and PS-388 Leukemia cell line data for the pentapeptideamides (18), (20–22) and (24).

| | Cell type | Cell line | 18 | 20 | 21 | 22a |
|---|---|---|---|---|---|---|
| GI-50 (µg/ml) | Ovarian | OVCAR-3 | $5.1 \times 10^{-2}$ | $9.9 \times 10^{-3}$ | $3.5 \times 10^{-3}$ | $1.5 \times 10^{-2}$ |
| | CNS | SF-2X5 | $1.4 \times 10^{-1}$ | $6.7 \times 10^{-3}$ | $3.8 \times 10^{-3}$ | $7.7 \times 10^{-2}$ |
| | Renal | A4X8 | $1.6 \times 10^{-1}$ | $2.7 \times 10^{-2}$ | $2.0 \times 10^{-2}$ | $8.8 \times 10^{-2}$ |
| | Lung-NSC | NCI-H460 | $2.1 \times 10^{-1}$ | $3.3 \times 10^{-2}$ | $2.2 \times 10^{-3}$ | $3.2 \times 10^{-2}$ |
| | Colon | KM20L2 | $2.4 \times 10^{-1}$ | $2.8 \times 10^{-2}$ | $2.1 \times 10^{-2}$ | $3.4 \times 10^{-2}$ |
| | Melanoma | SK-MEL-5 | $2.9 \times 10^{-1}$ | $2.5 \times 10^{-2}$ | $8.7 \times 10^{-3}$ | $3.0 \times 10^{-2}$ |
| TGI (µg/ml) | Ovarian | OVCAR-3 | $2.4 \times 10^{-1}$ | $5.7 \times 10^{-2}$ | $2.6 \times 10^{-2}$ | $7.6 \times 10^{-2}$ |
| | CNS | SF-2X5 | $4.3 \times 10^{-1}$ | $3.5 \times 10^{-2}$ | $>3.5 \times 10^{-2}$ | $>1$ |
| | Renal | A4X8 | $5.2 \times 10^{-1}$ | $4.5 \times 10^{-1}$ | $>1$ | $>1$ |
| | Lung-NSC | NCI-H460 | $6.6 \times 10^{-1}$ | $3.4 \times 10^{-2}$ | $2.1 \times 10^{-2}$ | $1.3 \times 10^{-1}$ |
| | Colon | KM20L2 | $6.7 \times 10^{-1}$ | $1.2 \times 10^{-1}$ | $2.3 \times 10^{-1}$ | $1.5 \times 10^{-1}$ |
| | Melanoma | SK-MEL-5 | $>1$ | $6.1 \times 10^{-2}$ | $>1$ | $9.2 \times 10^{-1}$ |
| LC-50 (µg/ml) | Ovarian | OVCAR-3 | $9.9 \times 10^{-1}$ | $>1$ | $>1$ | $>1$ |

TABLE 1-continued

Human Cancer-Cell line and PS-388 Leukemia cell line data for the pentapeptideamides (18), (20–22) and (24).

|  | Cell type | Cell line |  |  |  |  |
|---|---|---|---|---|---|---|
|  | CNS | SF-2X5 | >1 | >1 | >1 | >1 |
|  | Renal | A4X8 | >1 | >1 | >1 | >1 |
|  | Lung-NSC | NCI-H460 | >1 | >1 | >1 | >1 |
|  | Colon | KM20L2 | >1 | >1 | >1 | >1 |
|  | Melanoma | SK-MEL-5 | >1 | >1 | >1 | >1 |
| ED-50 (µg/ml) | Mouse Leukemia | PS-388 | >1 | $3.93 \times 10^{-1}$ | $2.97 \times 10^{-2}$ | >1 |

|  | Cell type | Cell line | 22b | 22c | 24 |
|---|---|---|---|---|---|
| GI-50 (µg/ml) | Ovarian | OVCAR-3 | $3.1 \times 10^{-2}$ | $3.1 \times 10^{-3}$ | $1.6 \times 10^{-2}$ |
|  | CNS | SF-2X5 | $2.7 \times 10^{-1}$ | $2.6 \times 10^{-2}$ | $7.2 \times 10^{-3}$ |
|  | Renal | A4X8 | $2.5 \times 10^{-1}$ | $2.3 \times 10^{-2}$ | $3.6 \times 10^{-2}$ |
|  | Lung-NSC | NCI-H460 | $9.6 \times 10^{-2}$ | $5.4 \times 10^{-3}$ | $3.5 \times 10^{-2}$ |
|  | Colon | KM20L2 | $1.3 \times 10^{-1}$ | $1.1 \times 10^{-2}$ | $3.4 \times 10^{-2}$ |
|  | Melanoma | SK-MEL-5 | $9.1 \times 10^{-2}$ | $7.3 \times 10^{-3}$ | $3.2 \times 10^{-2}$ |
| TGI (µg/ml) | Ovarian | OVCAR-3 | $1.3 \times 10^{-1}$ | $1.4 \times 10^{-2}$ | $1.1 \times 10^{-1}$ |
|  | CNS | SF-2X5 | >1 | >1 | $5.3 \times 10^{-2}$ |
|  | Renal | A4X8 | >1 | $6.0 \times 10^{-1}$ | >1 |
|  | Lung-NSC | NCI-H460 | $5.7 \times 10^{-1}$ | $4.4 \times 10^{-2}$ | $2.1 \times 10^{-1}$ |
|  | Colon | KM20L2 | $7.2 \times 10^{-1}$ | $1.2 \times 10^{-1}$ | $2.0 \times 10^{-1}$ |
|  | Melanoma | SK-MEL-5 | >1 | $3.1 \times 10^{-1}$ | $1.1 \times 10^{-1}$ |
| LC-50 (µg/ml) | Ovarian | OVCAR-3 | >1 | $6.1 \times 10^{-1}$ | >1 |
|  | CNS | SF-2X5 | >1 | >1 | >1 |
|  | Renal | A4X8 | >1 | >1 | >1 |
|  | Lung-NSC | NCI-H460 | >1 | >1 | >1 |
|  | Colon | KM20L2 | >1 | >1 | >1 |
|  | Melanoma | SK-MEL-5 | >1 | >1 | >1 |
| ED-50 (µg/ml) | Mouse Leukemia | PS-388 | $4.64 \times 10^{-1}$ | $7.0 \times 10^{-1}$ | $2.35 \times 10^{-1}$ |

To further aid in the understanding of the present invention, and not by way of limitation, the following Examples are presented.

EXAMPLE I

N-tert-butoxycarbonyl amino acid esters are synthesized as shown below following General Procedure A.

EXAMPLE I-a

Synthesis of trans-t-Boc-desmethoxy-desmethyldehydro-dolaproine ethyl ester (3a).

Reaction of the prolinal (1) with the phosphorane (2a) followed by purification on a SILICA GEL column with 1:3 acetone-hexane as the eluent gave an oily compound identified as the trans ester (3a, 64%); $R_f$=0.44 (3:1 Hexane-ethyl acetate); IR(neat): 2978, 2880, 1719, 1697, 1653, 1393, 1366, 1300, 1263, 1169, 1121, 1044 and 980 cm$^{-1}$; $^1$H NMR (300 MHz, CDCl$_3$): 6.72–6.88 (m, 1H, β CH=), 5.79(d, J=15.4 Hz, α=CH—CO), 4.30–4.50(m, 1H, CH—N), 4.16(q, J=6.7Hz, 2H, CH$_2$), 3.40(brm, 2H, CH$_2$—N), 1.95–2.10 (m, 1H, HCH), 1.70–1.90 (m, 3H, HCH, 2×CH$_2$), 1.4 (s, 9H, t-Bu) and 1.25(t, 3H, CH$_2$—CH$_3$); EIMS (m/z): 269(M$^+$), 213, 196, 169, 140(100%), 114, 96, 81, 70 and 57.

Only traces of the cis- ester was formed in the reaction.

EXAMPLE I-b

Synthesis of trans-t-Boc-desmethoxy-dehydro-dolaproine ethyl ester (3b).

Reaction of the prolinal (1) with the phosphorane (2b) followed by purification on a SILICA GEL column with 1:4 acetone-hexane as the eluent gave, followed by a mixture of the cis- and trans- esters (16%), an oily compound identified as the trans-ester (3b, 50%); $R_f$=0.46 (4:1 hexane-acetone); [α]$_D^{25}$=−7.7° (c 0.35, CHCl$_3$); IR(neat): 2976, 2932, 2876, 1717, 1699, 1653, 1635, 1506, 1476, 1456, 1437, 1395, 1366, 1317, 1256, 1238, 1167, 1138, 1115, 1096, 1034, 774 and 748 cm$^{-1}$; $^1$H NMR(300MHz, CDCl$_3$): 6.62(m, 1H, =CH), 4.40–4.60 (m, 1H, NCH), 4.19 (q, J=6.8Hz, 2H, COCH$_2$), 3.35–3.55 (m, 2H, NCH$_2$), 2.10–2.18 (m, 1H, HCH), 1.8–2.0 (m, 2H, CH$_2$), 1.884(brs, 3H, =C(CH$_3$)), 1..6–1.7(m, 1H, HCH), 1.4(brs, 9H, t-Bu) and 1.29(t, J=6.8Hz, 3H, CH$_2$CH$_3$); EIMS (m/z): 283(M$^+$), 227, 210, 183, 154(100%), 136, 110, 93, 80, 70 and 57.

EXAMPLE II

Synthesis of t-Boc-desmethoxy-desmethyl-dolaproine ethyl ester (4)

A solution of the unsaturated ester (3a, 0.48 mmol) was stirred with 10% Pd-C (25 mg), in ethanol, under an atmosphere of hydrogen (in a balloon) for 24 hours. Removal of the catalyst and the solvent left behind an oily residue of the saturated ester (4, 97%); $R_f$=0.53 (3:1 hexane-acetone); IR(neat): 2976, 2934, 2878, 1736, 1696, 1154, 1395, 1256, 1173, 1101, 1038, 910, 864 and 773 cm$^{-1}$; $^1$H NMR(300 MHz, CDCl$_3$): 4.10 (q, J=7.2Hz, 2H, OCH$_2$), 3.70–3.85(m, 1H, CH—N), 3.20–3.45(m, 2H, CH$_2$N), 2.27(brt, 2H, CH$_2$—CO), 1.52–1.95(m, 6H, 3×CH$_2$), 1.43(s, 9H, t-Bu) and 1.22, 1.21(t, J=7Hz, 3H, Me—CH$_2$); EIMS (m/z): 269(M$^+$—2H), 213, 196, 169, 140, 124, 114, 96, 82, 70 and 57(100%)

EXAMPLE III

The hydrolysis of the dolaproine ethyl esters (3a–b, 4) gave the results shown below when General procedure B was followed.

EXAMPLE III-a

Hydrolysis of trans-t-Boc-desmethoxy-desmethyldehydrodolaproine (5a).

Hydrolysis of the ester (3a) with LiOH gave an oily compound identified as the free acid (5a, 66%); $R_f$=0.66(3:2 acetone-hexane with one drop of acetic acid); $[\alpha]_D^{25}$=−54.7° (c 0.15, CHCl$_3$); IR(neat): 3167, 2976, 2932, 2884, 1697, 1653, 1395, 1256, 1165, 1126, 980, 860 and 773 cm$^{-1}$; $^1$H NMR(300 MHz, CDCl$_3$): 6.86–6.93 (m, 1H, β CH=), 5.81 (d, J=15.6Hz, 1H, α =CH—CO), 4.34–4.50 (m, 1H, CH—N), 3.32–3.43 (m, 2H, CH$_2$—N), 1.95–2.20 (m, 1H, HCH), 1.70–1.90(m, 3H, HCH, CH$_2$) and 1.43, 1.39(s, 9H, t-Bu); EIMS (m/z): 241(M$^+$), 210, 185, 168, 140, 124, 113, 96, 79, 70 and 57(100%).

EXAMPLE III-b

Hydrolysis of trans-t-boc-desmethoxy-dehydro-dolaproine (5b).

Hydrolysis of the ester (3b) with LiOH followed by purification led to the free acid (5b, 93%); $^1$H NMR(300 MHz, CDCl$_3$): 6.77 (d, J=8.8Hz, 1H, =CH), 4.4–4.6 (m, 1H, NCH), 3.4–3.6 (m, 2H, NCH$_2$), 2.1–2.2(m, 1H, HCH), 1.8–2.0(m, 2H, CH$_2$), 1.90(brs, 3H, =C(CH$_3$)), 1.6–1.75(m, 1H, HCH) and 1.41(brs, 9H, t-Bu); MS: 255 (M$^+$), 227, 199, 182, 154, 136, 110 97, 83, 70 and 57 (100%).

EXAMPLE III-c

Hydrolysis of t-Boc-desmethoxy-desmethyl-dolaproine (5c).

Hydrolysis of the ester (4) with LiOH gave of the free acid (5c, 99%); $R_f$=0.59 (3:2 acetone-hexane with 1 drop of acetic acid); $[\alpha]_D^{25}$=−6.67° (c 0.3, CHCl$_3$); IR(neat): 3441(br), 2972, 2932, 2878, 1694, 1587, 1416, 1366, 1252, 1171, 1105, 912, 858 and 711 cm$^{-1}$; $^1$H NMR(300 MHz, CDCl$_3$): 3.75–3.80(brm, 1H, CH—N), 3.16–3.30(brm, 2H, CH$_2$—N), 1.99–2.24(m, 4H, 2×CH$_2$), 1.70–1.85(m, 2H, CH$_2$), 1.55–1.65(m, 1H, HCH), 1.40(s, 9H, t-Bu) and 1.18–1.38 (m, 1H, HCH); EIMS (m/z): 243(M$^+$), 225, 210, 186, 170, 149, 142, 126, 114, 97, 78, 70 and 57(100%).

EXAMPLE IV

Synthesis of t-Boc-dolaproine methyl ester (7).

To a solution of t-boc-dolaproine (6, 0.2 mmol) in dry THF (1 mL) was added NaHCO$_3$ (0.4 mmol) followed by methyl iodide (150 mg) and the suspension was stirred in an argon atmosphere for 24 hours. The t.l.c. of the mixture (3:1 hexane-acetone) indicated the formation of the ester. Water (50 mL) was added and the solution was extracted with ethyl acetate (3×20 mL). The organic phase was washed with water, dried and concentrated in vacuum to obtain an oily residue which was chromatographed over a SILICA GEL column (3:1 hexane-acetone) to obtain the pure ester as an oil (7, 92%); Rf=0.65 (3:1 hexane-acetone); $[\alpha]_D^{25}$=−50.8° (c 0.38, CHCl$_3$); IR(neat): 2974, 2934, 2880, 1736, 1697, 1456, 1396, 1259, 1165, 1099, 870 and 771 cm$^{-1}$; $^1$H NMR(300 MHz, CDCl$_3$): 1.22(d, J=7Hz, 3H, CH—Me), 1.46(s, 9H, t-Bu), 1.63–1.95(m, 4H, 2×CH$_2$), 2.5 (m, 1H, CH—CO), 3.16–3.23 (m, 1H, CH—OMe), 3.40 (s, 3H, OMe), 3.49–3.78 (m, 3H, N—CH$_2$, a-H) and 3.65 (s, 3H, COOMe); EIMS (m/z): 269(M$^+$-MeOH), 228, 196, 170, 158, 138, 131, 114, 98, 85, 82, 75, 70(100%) and 57.

EXAMPLE V

The synthesis of the dipeptides (9a–c) was accomplished as shown below following General Procedure C.

EXAMPLE V-a

Synthesis of trans-t-Boc-desmethoxy-desmethyl-dehydrodolaproine-methionine methyl ester (9a).

Reaction of the acid (5a) with methionine (8), following the General Procedure C, gave, after purification on a SILICA GEL column with 1:1 hexane-ethyl acetate as the eluent, the required dipeptide as a thick oil (9a, 85%); $R_f$=0.30 (1:1 hexane-ethyl acetate); $[\alpha]_D^{25}$=−16.2° (c 1.23, CHCl$_3$); IR(neat): 3298, 2974, 2928, 2880, 1746, 1694, 1645, 1541, 1395, 1366, 1262, 1202, 1167, 1119, 980, 858 and 772 cm$^{-1}$; $^1$H NMR(300 MHz, CDCl$_3$): 6.67–6.73(m, 1H, β CH=), 6.19(d, J=7.7Hz, 1H, α =CH—CO), 5.75–5.89(m, 1H, NH), 4.76(m, 1H, met CH—N), 4.30–4.50(m, 1H, pro CH—N), 3.7(s, 3H, OMe), 3.30–3.45(m, 2H, CH$_2$—N), 2.50(m, 2H, CH$_2$—S), 2.06(s, 3H, SMe), 1.60–2.20(m, 6H, 3×CH$_2$) and 1.416, 1,394(s, 9H, t-Bu); EIMS (m/z): 386(M$^+$), 330, 313, 286, 269, 256, 239, 225, 212, 193, 180, 162, 142, 124(100%), 114, 96, 81, 70 and 57.

EXAMPLE V-b

Synthesis of trans-t-Boc-desmethoxy-dehydrodolaproine-methionine methyl ester (9b).

Reaction of the acid (5b) with methionine (8), following the General Procedure C, gave, after purification on a SILICA GEL column with 2:1 hexane-ethyl acetate as the eluent, the required dipeptide as a thick oil (9b, 79%); $R_f$=0.19 (1:1 hexane-ethyl acetate); $[\alpha]_D^{25}$=−4.2° (c 0.31, CHCl$_3$); IR(neat): 3335, 2972, 2924, 2878, 1744, 1695, 1670, 1626, 1539, 1395, 1366, 1169 and 1115 cm$^{-1}$; NMR(300 MHz, CDCl$_3$): 6.45–6.53(m, 1H, CH=), 6.20–6.35(m, 1H, NH), 4.74 (m, 1H, met CH—N), 4.40–4.60 (m, 1H, pro CH—N), 3.74(s, 3H, OMe), 3.30–3.50(m, 2H, CH$_2$—N), 2.50(m, 2H, CH$_2$—S), 2.07(s, 3H, SMe), 1.75–2.20(m, 5H, 2×CH$_2$, HCH), 1.58(brs, 3H, CH$_2$), 1.58–1.68(m, 1H, HCH) and 1.40(s, 9H, t-Bu); EIMS (m/z): 400(M$^+$), 327, 270, 226, 181, 138(100%) and 109.

EXAMPLE V-c

Synthesis of t-Boc-desmethoxy-desmethyl-dolaproine-methionine methyl ester (9c).

Reaction of the acid (5c) with methionine (8) following the General Procedure C and purification of the residue obtained on a SILICA GEL column with 1:3 acetone-hexane as the eluent gave the required dipeptide as a thick oil (9c, 58%); $R_f$=0.36 (1:3 acetone-hexane); $[\alpha]_D^{25}$=−4.8° (c 0.23, CHCl$_3$); IR(neat): 3295, 2971, 2930, 2878, 1748, 1692, 1541, 1397, 1366, 1256, 1171, 1117 and 772 cm$^{-1}$; $^1$H NMR(300 MHz, CDCl$_3$): 8.14(d, J=7.2Hz, 1H, NH), 4.61(brq, 1H, met CH—N), 3.29(brq, 1H, pro CH—N), 3.71(s, 3H, OMe), 3.29(m, 2H, CH$_2$—N), 2.56(t, J=7.4Hz, 2H, CH$_2$—S), 2.08(s, 3H, SMe), 1.80–2.40(m, 6H, 3×CH$_2$), 1.55–1.70(m, 4H, 2×CH$_2$) and 1.43(s, 9H, t-Bu); EIMS (m/z): 388(M$^+$), 314, 287, 258, 214, 182, 145, 124, 84, 70(100%) and 57.

EXAMPLE VI-a

Synthesis of the trifluoroacetate salts (14–16).

Reaction of the compounds (3b, 7, 9-a–c) with the trifluoroacetic acid following the General Procedure D gave the trifluoroacetate salts (14–16).

EXAMPLE VI-b

Synthesis of Z-Val-Dil-COOH (13).

Deprotection the t-boc group in the dipeptide (12) with trifluoroacetic acid following the General Procedure D gave the free acid (13, 98.8%); $R_f$=0.68 (2:1 acetone-hexane with 1 drop of acetic acid); $[\alpha]_D^{25}$=–4.7° (C 0.19, CHCl$_3$); IR(neat): 3290, 2966, 2935, 2877, 2831, 1716, 1635, 1610, 1523, 1498, 1456, 1415, 1296, 1261, 1236, 1180, 1138, 1097, 1027, 723 and 698 cm$^{-1}$; $^1$H NMR (300 MHz, CDCl$_3$): 7.2–7.4 (m, 5H, Ph), 6.001(m, 1H, —NH), 5.10(s, 2H, CH$_2$—Ph), 4.6–4.8 (m, 1H, Val CH—N), 4.48 (dd, J=9.0 and 6.9 Hz, 1H, dil CH—N), 3.88(m, 1H, CH—OCH$_3$), 3.36(s, 1H, OCH$_3$), 3.04(s, 3H, N—CH$_3$), 2.4–2.6(m, 2H, CH$_2$—COOH), 1.95–2.01(m, 1H, CH), 1.3–1.4 (m, 1H, CH), 0.93–1.08 (three ds and a multiplet, 3×CH$_3$, CH$_2$-CH$_3$) and 0.82(t, J=7.4Hz, 3H, CH$_2$-CH$_3$).

EXAMPLE VII

Synthesis of the human cancer active peptides (18), (20–22), (24) took place as shown below following General Procedures E and F.

EXAMPLE VII-a

Z-Val-Dil-Dap-Phenethylamine (18).

Coupling of the Dap-phenethylamine trifluoroacetate salt (17) with Z-val-dil free acid (13) following the General Procedure E and chromatography of the residue with 2:3 hexane acetone to obtain the required tripeptide, Z-val-dil-dap-phenethylamine (18, 86%); $R_f$=0.22 (1:1 hexane-acetone); m.p.=44°–46° C.; $[\alpha]_D^{25}$ =–20.7° (c 0.14, CHCl$_3$); IR(thin film): 3306, 2965, 2934, 2878, 2832, 1717, 1638, 1539, 1454, 1416, 1233, 1099, 1028, 741 and 698 cm$^{-1}$; MS: m/z 708(M$^+$), 676, 568, 488, 419, 375, 311, 276, 225, 186, 154, 100, 91(100%) and 70.

EXAMPLE VII-b trans-Dov-Val-Dil-desmethoxy-dehydro-dolaproine ethyl ester (20).

Coupling of the tripeptide-tfa salt (19) with desmethoxy dolaproine-tfa salt (14) following the General Procedure F and chromatography of the residue on a SILICA GEL column with 3:2 hexane-acetone as the eluent to obtain the required tetrapeptide (20, 86%); m.p.=42°–44° C.; $R_f$=0.34 (3:2 hexane-acetone); $[\alpha]_D^{25}$=–45.6° (c 0.27, CHCl$_3$); IR(neat): 3293, 2963, 2932, 2874, 2830, 1713, 1643, 1447, 1416, 1256, 1099, 1036 and 748 cm$^{-1}$; EIMS (m/z): 594(M$^+$), 551, 519, 462, 369, 311, 268, 227, 182, 138, 100(100%) and 57.

EXAMPLE VII-c

Dov-Val-Dil-Dap methyl ester (21).

Coupling of the tripeptide-tfa salt (19) with dap-methyl ester trifluoroacetate salt (15) following the General Procedure F and chromatography of the residue on a SILICA GEL column with 3:2 hexane-acetone as the eluent gave the required tetrapeptide (21, 96.7%); $R_f$=0.52 (3:2 hexane-acetone); $[\alpha]_D^{25}$=–118.3° (c 0.12, CHCl$_3$); IR(neat): 3283, 3163, 2961, 2928, 1734, 1653, 1618, 1456, 1406, 1261, 1142 and 1095 cm$^{-1}$; EIMS (m/z): 612(M$^+$), 597, 569, 481, 449, 412, 387, 324, 286, 227, 186, 154 and 128.

EXAMPLE VII-d trans-Dov-val-dil-desmethoxy desmethyl dehydrodolaproine-methionine methyl ester (22a).

Coupling of the tripeptide-tfa salt (19) with trans-desmethoxy-desmethyl-dehydrodolapoine-methionine methyl ester trifluoroacetate salt (16a) following the General Procedure F and chromatography of the residue on a SILICA GEL column with 3:2 hexane-acetone as the eluent gave the required pentapeptide as a white solid (22a, 68%); $R_f$=0.53 (3:2 acetone-hexane); m.p.=78°–80° C.; $[\alpha]_D^{25}$=–34.3° ; IR(neat): 3298, 2963, 2932, 2876, 1744, 1626, 1532, 1447, 1202, 1098 and 984 cm$^{-1}$; EIMS (m/z): 697(M$^+$), 682, 66, 654, 638, 623, 565, 522, 472, 441, 414, 371, 325, 313, 298, 287, 269, 239, 227, 210, 199, 186, 154, 136, 124 and 101(100%).

EXAMPLE VII-e trans-Dov-val-dil-desmethoxy dehydrodolaproine-methionine methyl ester (22b).

Coupling of the tripeptide-tfa salt (19) with trans-desmethoxy dehydrodolapoine-met-methyl ester trifluoroacetate salt (16b) following the General Procedure F and chromatography of the residue on a SILICA GEL column with 3:1 hexane-acetone as the eluent gave the required pentapeptide as a white solid (22b, 53.2%); $R_f$=0.74 (3:2 acetone-hexane); m.p.=73°–75° C.; $[\alpha]_D^{25}$=–29.2° (C 0.13, CHCl$_3$); IR(neat): 3306, 2963, 2932, 2874, 2830, 2787, 1745, 1626(br), 1524, 1445, 1418, 1202, 1171 and 1097 cm$^{-1}$; EIMS (m/z): 711(M$^+$), 696, 680, 668, 652, 637, 612, 569, 536, 486, 462, 450, 439, 428, 412, 386, 385, 370, 327, 299, 283, 267, 253, 227, 199, 186, 184, 155, 154, 138, 136, 128 and 101(100%).

EXAMPLE VII-f

Dov-val-dil-desmethoxy-desmethyl-dolaproine-methionine methyl ester (22c).

Coupling of the tripeptide-tfa salt (19) with trans-desmethoxy-desmethyl-dolaproine-met-methyl ester trifluoroacetate salt (16c) following the General Procedure F and chromatography of the residue on a SILICA GEL column with 3:2 hexane-acetone as the eluent gave the required pentapeptide as a white solid (22c, 78%); $R_f$=0.49 (3:2 acetone-hexane); m.p.=34°–36° C.; $[\alpha]_D^{25}$=–6.1° (C 0.18, CHCl$_3$); IR(neat): 3297, 2961, 2932, 2874, 2830, 1748, 1622, 1540, 1456, 1202, 1171, 1098 and 1038 cm$^{-1}$; EIMS (m/z): 699(M$^+$), 684, 668, 656, 640, 625, 608, 582, 557, 524, 495, 474, 442, 427, 411, 373, 359, 327, 311, 287, 271, 241, 227, 199, 186, 184, 164, 155, 154, 128, 126, 124 and 101(100%).

EXAMPLE VII-g

Dov-Val-Dil-Doe (24).

Coupling of the tripeptide-tfa salt (19) with dolaphenine-tfa salt (23) following the General Procedure F and chromatography of the residue on a SILICA GEL column with 2:3 acetone-hexane as the eluent gave the required tetrapeptide as a white solid (24, 87%); m.p.=131°–133° C.; $R_f$=0.40 (3:2 hexane-acetone); $[\alpha]_D^{25}$=–37.2° (c 0.25, CHCl$_3$); IR(neat): 3298, 2963, 2932, 2874, 2830, 2787, 1624, 1524, 1499, 1466, 1414, 1370, 1202, 1098, 733 and 700 cm$^{-1}$; EIMS (m/z): 615(M$^+$), 600, 572, 540, 524, 492, 473, 441, 424, 412, 390, 358, 343, 327, 301, 290, 275, 258, 227, 199, 188, 170, 154, 140, 128, 113, 100(100%), 85, 72 and 55.

Thus, the synthesis of these seven pentapeptides, which are structural modifications of dolastatin 10, has been shown. These peptides are more easily synthesized than dolastatin 10 and, like dolastatin 10, exhibit effective antineoplastic activity against various human tumor (L1210) and mouse leukemia (P-388) cell lines thus rendering these seven peptides extremely important as possible replacements for dolastatin 10.

From the foregoing, it is readily apparent that a useful embodiment of the present invention has been herein described and illustrated which fulfills all of the aforestated objectives in a remarkably unexpected fashion. It is, of course, understood that such modifications, alterations and adaptations as may readily occur to the artisan confronted with this disclosure are intended within the spirit of this disclosure which is limited only by the scope of the claims appended hereto.

What is claimed:

1. A composition of matter having the structural formula:

wherein: $R_1$ is selected from the group consisting of:

$R_2$ is selected from the group consisting of:

and and $R_3$ is selected from the group consisting of hydrogen and methyl.

2. A composition of matter having the structural formula:

3. A composition of matter according to claim 1 wherein $R_1$ is:

and $R_2$ is:

4. A composition of matter according to claim 1 wherein $R_1$ is:

and $R_2$ is:

and R3 is selected from the group consisting of hydrogen and methyl.

5. A composition of matter according to claim 1 wherein $R_1$ is:

and $R_2$ is:

6. A composition of matter according to claim 1 wherein $R_1$ is:

and $R_2$ is:

7. A composition of matter according to claim 1 wherein $R_1$ is:

* * * * *